United States Patent [19]

Suzuki et al.

[11] Patent Number: 5,578,625
[45] Date of Patent: Nov. 26, 1996

[54] ACARICIDE

[75] Inventors: Junji Suzuki, Suzaka; Yasuo Kikuchi, Nagano; Tatsuya Ishida, Nagano; Tatsufumi Ikeda, Nagano, all of Japan

[73] Assignee: Yashima Chemical Industrial Co., Ltd., Kanagawa, Japan

[21] Appl. No.: 347,443

[22] PCT Filed: Jun. 11, 1993

[86] PCT No.: PCT/JP93/00783

§ 371 Date: Dec. 5, 1994

§ 102(e) Date: Dec. 5, 1994

[87] PCT Pub. No.: WO93/25079

PCT Pub. Date: Dec. 23, 1993

[30] Foreign Application Priority Data

Jun. 12, 1992 [JP] Japan ................................. 4-177737

[51] Int. Cl.$^6$ .................................................... A01N 43/76
[52] U.S. Cl. ................................................................ 514/374
[58] Field of Search ............................................. 514/374

[56] References Cited

U.S. PATENT DOCUMENTS 4,977,171 12/1990 Suzuki et al. ............................ 514/365
5,141,948 8/1992 Miyamoto et al. ...................... 514/365

FOREIGN PATENT DOCUMENTS 2-85268 3/1990 Japan.
3-232867 10/1991 Japan.

Primary Examiner—Allen J. Robinson
Attorney, Agent, or Firm—Wenderoth, Lind & Ponack

[57] ABSTRACT

An acaricide which contains as an effective ingredient an oxazoline or thiazoline compound represented by the following formula

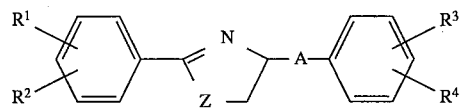

wherein, $R^1$, $R^2$, $R^3$, $R^4$, Z and A are as defined in the description.

This acaricide has an excellent acaricidal activity against house dust mites and mites and ticks which parasitize pets or wild animals or birds.

3 Claims, No Drawings

ACARICIDE

This application is a 371 of PCT/JP93/00783 filed Jun. 11, 1993.

TECHNICAL FIELD

This invention relates to an agent for control of mites and ticks as an environmental pest, and specifically relates to an acaricide which contains an oxazoline or thiazoline compound as an effective ingredient, and displays an excellent control effect against house dust mites and mites and ticks which parasitize pets or wild animals or birds.

BACKGROUND ART

Oxazoline or thiazoline compounds, which mainly target mites which parasitize crops, are disclosed in Japanese Laid-Open Patent Publication Nos. 85268/1990 and 23287/1991. However, there is no disclosure in the above publications about control effect on mites which live in houses or mites which parasitize large or small animals or birds, etc.

Under the above circumstances, the object of this invention lies in developing a new use of some particular compounds among compounds which conceptionally included in the above official gazettes, and searching compounds capable of displaying an excellent control effect against mites as an environmental pest among the selected compounds.

DISCLOSURE OF INVENTION

The present inventors, for the purpose of fulfilling the above requisites, tested novel compounds invented as an agricultural acaricide on dust mites in houses and mites and ticks which parasitize livestock, and as a result found that these compounds show an extremely excellent acaricidal effect against them.

Namely, this invention is an acaricide, which contains as an effective ingredient an oxazoline or thiazoline compound represented by the following formula

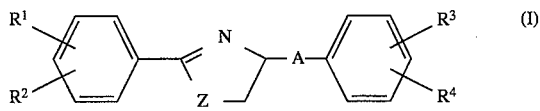

wherein, $R^1$ and $R^2$ are the same or different, and each denote a hydrogen atom, a halogen atom, a lower alkyl group, a lower alkoxy group, a nitro group, a trifluoromethyl group or a trifluoromethoxy group, $R^3$ and $R^4$ each denote a hydrogen atom, a halogen atom, a trifluoromethyl group, a trifluoromethoxy group, an alkyl group having 1 to 20 carbon atoms, an alkoxy group having 1 to 20 carbon atoms, an alkylthio group having 1 to 20 carbon atoms, a lower alkoxy-lower alkyl group, a lower alkoxy-lower alkoxy group, an alkenyloxy group having 3 or more carbon atoms, a lower alkynyloxy group, a tri(lower alkyl)silyl group, a cycloalkyl group optionally substituted with a lower alkyl group or a group

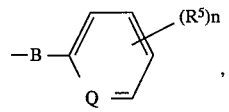

B denotes a direct bond, an oxygen atom, a lower alkylene group, a lower alkyleneoxy group, a lower alkylenedioxy group or a di(lower alkyl)silyl group, Q denotes CH or a nitrogen atom, n denotes an integer of 0 to 5, $R^5$ substituents, whose number is n, are the same or different, and each denote a halogen atom, a lower alkyl group, a lower alkoxy group, a lower haloalkyl group, a lower haloalkoxy group or a tri(lower alkyl)silyl group, A denotes a direct bond or a lower alkylene group, and Z denotes an oxygen atom or a sulfur atom.

In the present description, the term "lower" means that the number of carbon atoms of a group or compound to which this term was attached is 6 or less. The "halogen atom" denotes a fluorine atom, a chlorine atom, a bromine atom or an iodine atom; the "alkyl group" denotes a straight-chain or branched alkyl group having 1 to 20, preferably 1 to 15 carbon atoms; the "alkoxy group" and the "alkylthio group" respectively denote an (alkyl)-O-group and an (alkyl)-S-group whose respective alkyl parts have the above meaning; and the "haloalkyl group" denotes an alkyl group at least one of whose hydrogen atoms bound to the carbon atoms is replaced with a halogen atom, such as, for example, chloromethyl, trifluoromethyl or trifluoroethyl. The "haloalkoxy group" denotes a (haloalkyl)-O-group wherein the haloalkyl part has the above meaning, such as, for example, a trifluoromethoxy group; and the "lower alkoxy-lower alkyl group" is a (lower alkyl)-O-(lower alkyl) group wherein each alkyl part has the above meaning, and includes, for example, ethoxymethyl, n-propoxymethyl, isopropoxymethyl, n-butoxymethyl, isobutoxymethyl, 2-methoxyethyl, 2-ethoxyethyl groups, etc.

The "lower alkoxy-lower alkoxy group" is a (lower alkyl)-O-(lower alkyl)-O-group wherein each alkyl part has the above meaning, and includes, for example, 2-methoxyethoxy, 2-ethoxyethoxy, 2-n-propoxyethoxy, 4-isopropoxybutoxy groups, etc. The "alkenyloxy group" is an alkenyl group whose alkenyl part is straight-chain or branched chain, and denotes an alkenyloxy group having 3 to 15 carbon atoms such as, for example, an allyloxy, butenyloxy, 3-methyl-2-butenyloxy, geranyloxy, farnesyloxy or citronellyloxy group; and as the "lower alkynyloxy group" can, for example, be exemplified a propargyloxy group. The "tri(lower alkyl)silyl group" includes, for example, trimethylsilyl, ethyldimethylsilyl, n-propyldi-methylsilyl, t-butyldimethylsilyl, triethylsilyl, methyldiethylsilyl groups, etc.

The "cycloalkyl group" includes those having 3 to 8 carbon atoms, e.g. a cyclohexyl group, and this cycloalkyl group may optionally be substituted with lower alkyl group(s). As examples of the thus substituted cycloalkyl groups can be mentioned methylcyclohexyl, ethylcyclohexyl, t-butylcyclohexyl groups, etc. The "lower alkylene group" denotes a straight-chain or branched chain alkylene group having 1 to 6 carbon atoms, and includes, for example, methylene, ethylene, propylene, butylene, 1,1-dimethylmethylene, etc. The "lower alkyleneoxy group" and the "lower alkylenedioxy group" are a-(lower alkylene)-O-group or -O-(lower alkylene)-group and an -O-(lower alkylene)-O- group, respectively, wherein each alkylene part has the above meaning. As example of the "di(lower alkyl)silyl group" can be mentioned dimethylsilyl, diethylsilyl, methylethylsilyl groups, etc.

Examples of the compounds of the formula (I) used in the invention are shown in the following Table 1 and Table 2.

The physical property value in the table denotes the refractive index ($n_D^{25}$) or the melting point (°C.).

The abbreviations in the table mean the following meanings:

Me=Methyl, Et=Ethyl, Pr=Propyl,
Bu=Butyl, Ph=Phenyl

TABLE 1

| Compound No. | $R_1, R_2$ | Z | $R_3, R_4$ | Physical property value |
|---|---|---|---|---|
| 1 | 2-F | O | H | 57.0–60.0 |
| 2 | 2-Cl | O | H | 71.5–74.0 |
| 3 | 2-Br | O | H | 101.0–103.5 |
| 4 | 2-I | O | H | 1.6244 |
| 5 | 2,6-diCl | O | H | 1.5987 |
| 6 | 2-Cl, 4-$NO_2$ | O | H | 38.5–41.0 |
| 7 | 2-F | O | 2-Cl | 117.0–121.0 |
| 8 | 2-Cl | O | 2-Cl | 1.6093 |
| 9 | 2-Br | O | 2-Cl | 53.0–55.0 |
| 10 | 2-Cl | O | 3-Cl | 1.6093 |
| 11 | 2-Cl | O | 4-Cl | 1.6075 |
| 12 | 2-Br | O | 4-Cl | 1.6072 |
| 13 | 2-Cl | O | 2-Br | 1.6213 |
| 14 | 2-Cl, 6-F | O | 4-Cl | 1.5814 |
| 15 | 2-Cl, 6-F | O | 4-F | 1.5654 |
| 16 | 2,6-diCl | O | 4-Cl | 52.5–53.5 |
| 17 | 2,6-diF | O | 4-Cl | 1.5701 |
| 18 | 2,6-diF | O | 4-Br | 67.5–69.0 |
| 19 | 2-Cl | O | 4-$CF_3$ | 107.0–119.0 |
| 20 | 2-Cl, 6-F | O | 2-$CF_3$ | 1.5335 |
| 21 | 2-Cl, 6-F | O | 4-$CF_3$ | 1.5326 |
| 22 | 2,6-diF | O | 4-$CF_3$ | 73.0–77.0 |
| 23 | 2-Cl | O | 4-$OCF_3$ | 61.0–62.0 |
| 24 | 2,6-diF | O | 4-$OCF_3$ | 61.5–64.5 |
| 25 | 2,6-diF | O | 2,4-diF | 1.5452 |
| 26 | 2-Cl | O | 2,4-diCl | 117.0–129.5 |
| 27 | 4-$OCF_3$ | O | 2,6-diF | 76.0–77.5 |
| 28 | 2,6-diF | O | 2,4-diCl | 66.0–67.0 |
| 29 | 2,6-diF | O | 3,4-diCl | 86.5–88.0 |
| 30 | 2,6-diF | O | 2-F, 4-Cl | 65.0–67.0 |
| 31 | 2-Cl, 6-F | O | 3,5-diF | 1.5502 |
| 32 | 2-Cl | O | 4-OMe | 1.5004 |
| 33 | 2-Cl, 6-F | O | 4-OMe | 77.5–82.5 |
| 34 | 2,6-diF | O | 4-SMe | 1.5962 |
| 35 | 2,6-diF | O | 2-Me, 4-Cl | 1.5691 |
| 36 | 2,6-diF | O | 2-Me, 4-n-Octyl | 1.5349 |
| 37 | 2,6-diF | O | 3-Cl, 4-Me | 1.5695 |
| 38 | 2-Cl, 6-F | O | 3-Br, 4-OMe | 1.5892 |
| 39 | 2,6-diF | O | 2-OMe, 4-t-Bu | 76.0–77.5 |
| 40 | 2,6-diF | O | 2-OMe, 4-n-Octyl | 1.5356 |
| 41 | 2,6-diF | O | 2-OMe, 4-n-Nonyl | 1.5329 |
| 42 | 2,6-diF | O | 2-OMe, 4-n-Decyl | 1.5262 |
| 43 | 2,6-diF | O | 4-Et | 1.5576 |
| 44 | 2,6-diF | O | 4-OEt | 1.5578 |
| 45 | 2-Cl, 6-F | O | 4-OEt | 1.5719 |
| 46 | 2,6-diF | O | 2-OEt, 4-n-Nonyl | 1.5264 |
| 47 | 2,6-diF | O | 2-OEt, 4-t-Bu | 101.0–102.0 |
| 48 | 2-Cl, 6-F | O | 2-OEt, 4-t-Bu | 1.5500 |
| 49 | 2,6-diF | O | 2-OEt, 4-n-Octyl | 1.5292 |
| 50 | 2-Cl, 6-F | O | 2-F, 4-OEt | 1.5870 |
| 51 | 2-Cl, 6-F | O | 3-Cl, 4-OEt | 83.0–85.0 |
| 52 | 2-Cl, 6-Cl | O | 3-Br, 4-OEt | 63.0–66.0 |
| 53 | 2,6-diF | O | 4-n-Pr | 1.5474 |
| 54 | 2,6-diF | O | 4-i-Pr | 1.5512 |
| 55 | 2,6-diF | O | 3-O-i-Pr | 1.5504 |
| 56 | 2-Cl, 6-F | O | 4-O-n-Pr | 1.5631 |
| 57 | 2,6-diF | O | 4-O-i-Pr | 1.5504 |
| 58 | 2-Cl, 6-F | O | 4-O-i-Pr | 1.5635 |
| 59 | 2,6-diF | O | 4-S-i-Pr | 1.5758 |
| 60 | 2,6-diF | O | 2-O-n-Pr, 4-n-Pentyl | 1.5362 |
| 61 | 2,6-diF | O | 2-O-n-Pr, 4-t-Bu | 1.5349 |
| 62 | 2-Cl, 6-F | O | 2-Cl, 4-O-i-Pr | 1.5683 |
| 63 | 2,6-diF | O | 4-n-Bu | 102.5–105.0 |
| 64 | 2,6-diF | O | 4-i-Bu | 1.5447 |
| 65 | 2-Cl, 6-F | O | 4-i-Bu | 1.5558 |
| 66 | 2,6-diF | O | 4-sec-Bu | 1.5974 |
| 67 | 2,6-diF | O | 4-t-Bu | 1.5471 |
| 68 | 2-Cl, 6-F | O | 4-t-Bu | 1.5592 |
| 69 | 2,6-diMe | O | 4-t-Bu | 83.5–86.0 |

TABLE 1-continued

| Compound No. | $R_1, R_2$ | Z | $R_3, R_4$ | Physical property value |
|---|---|---|---|---|
| 70 | 2,6-diF | O | 4-O-n-Bu | 60.5–62.5 |
| 71 | 2-Cl, 6-F | O | 4-O-n-Bu | 55.0–56.0 |
| 72 | 2,6-diF | O | 4-O-i-Bu | 1.5446 |
| 73 | 2,6-diF | O | 4-O-sec-Bu | 1.5414 |
| 74 | 2,6-diF | O | 2-O-n-Bu, 4-t-Bu | 1.5316 |
| 75 | 2,6-diF | O | 2-Cl, 4-t-Bu | 1.5517 |
| 76 | 2,6-diF | O | 2-F, 4-O-n-Bu | 1.5350 |
| 77 | 2,6-diF | O | 4-n-Pentyl | 1.5445 |
| 78 | 2-Cl, 6-F | O | 4-n-Pentyl | 1.5527 |
| 79 | 2,6-diF | O | 4-i-Pr | 68.0–71.0 |
| 80 | 2-Cl, 6-F | O | 4-i-Pentyl | 1.5504 |
| 81 | 2,6-diF | O | 4-t-Pentyl | 1.5396 |
| 82 | 2-Cl, 6-F | O | 4-neo-Pentyl | 1.5543 |
| 83 | 2,6-diF | O | 4-O-n-Pentyl | 1.5378 |
| 84 | 2,6-diF | O | 4-O-i-Pentyl | 1.5396 |
| 85 | 2,6-diF | O | 2-O-n-Pentyl, 4-t-Bu | 1.5280 |
| 86 | 2,6-diF | O | 2-F, 4-n-Pentyl | 1.5274 |
| 87 | 2-Cl, 6-F | O | 2-F, 4-n-Pentyl | 1.5382 |
| 88 | 2,6-diF | O | 2-Cl, 4-n-Pentyl | 1.5435 |
| 89 | 2,6-diF | O | 4-n-Hexyl | 1.5531 |
| 90 | 2,6-diF | O | 4-i-Hexyl | 1.5372 |
| 91 | 2-Cl, 6-F | O | 4-i-Hexyl | 1.5486 |
| 92 | 2,6-diF | O | 4-O-n-Hexyl | 1.5350 |
| 93 | 2,6-diF | O | 2-O-n-Hexyl, 4-t-Bu | 1.5398 |
| 94 | 2,6-diF | O | 2-F, 4-n-Hexyl | 1.5272 |
| 95 | 2,6-diF | O | 2-Cl, 4-n-Hexyl | 1.5440 |
| 96 | 2,6-diF | O | 4-n-Heptyl | 1.5322 |
| 97 | 2-Cl, 6-F | O | 4-n-Heptyl | 1.5432 |
| 98 | 2,6-diF | O | 4-O-n-Heptyl | 1.5314 |
| 99 | 2-Cl, 6-F | O | 4-O-n-Heptyl | 1.5419 |
| 100 | 2-Cl, 6-F | O | 4-O—CH(di-n-Pr) | 1.5401 |
| 101 | 2,6-diF | O | 2-F, 4-n-Heptyl | 1.5236 |
| 102 | 2,6-diF | O | 2-Cl, 4-n-Hepyl | 1.5406 |
| 103 | 2-$CF_3$ | O | 4-n-Octyl | 1.5166 |
| 104 | 2,6-diF | O | 4-n-Octyl | 1.5226 |
| 105 | 2,6-diF | O | 4-O-n-Octyl | 1.5292 |
| 106 | 2,6-diF | O | 2-F, 4-n-Octyl | 1.5215 |
| 107 | 2-Cl, 6-F | O | 2-F, 4-n-Octyl | 1.5322 |
| 108 | 2,6-diF | O | 2-Cl, 4-n-Octyl | 1.5372 |
| 109 | 2,6-diF | O | 4-n-Nonyl | 1.5304 |
| 110 | 2-Cl, 6-F | O | 4-n-Nonyl | 1.5370 |
| 111 | 2,6-diF | O | 4-(1-Me-Octyl) | 1.5294 |
| 112 | 2,6-diF | O | 4-O-n-Nonyl | 1.5269 |
| 113 | 2,6-diF | O | 4-S-n-Nonyl | 1.5512 |
| 114 | 2,6-diF | O | 2-F, 4-n-Nonyl | 1.5184 |
| 115 | 2-Cl, 6-F | O | 2-F, 4-n-Nonyl | 1.5286 |
| 116 | 2,6-diF | O | 2-Cl, 4-n-Nonyl | 1.5283 |
| 117 | 2-Cl, 6-F | O | 4-O-(3,7-diMe-Octyl) | 1.5377 |
| 118 | 2,6-diF | O | 4-n-Decyl | 1.5241 |
| 119 | 2,6-diF | O | 4-O-n-Decyl | 1.5236 |
| 120 | 2,6-diF | O | 2-n-Decyl, 4-F | 1.5242 |
| 121 | 2,6-diF | O | 2-F, 4-n-Decyl | 1.5154 |
| 122 | 2,6-diF | O | 2-Cl, 4-n-Decyl | 1.5194 |
| 123 | 2,6-diF | O | 4-(4,8-diMe-Nonyl) | 1.5315 |
| 124 | 2-Cl, 6-F | O | 4-O-n-Undecyl | 1.5310 |
| 125 | 2,6-diF | O | 2-F, 4-n-Undecyl | 1.5150 |
| 126 | 2,6-diF | O | 4-n-Dodecyl | 1.5194 |
| 127 | 2-Cl, 6-F | O | 4-O-n-Dodecyl | 1.5268 |
| 128 | 2,6-diF | O | 2-F, 4-n-Dodecyl | 1.5106 |
| 129 | 2,6-diF | O | 4-O-n-Tridecyl | 43.0–45.0 |
| 130 | 2,6-diF | O | 4-O-n-Tetradecyl | 42.5–45.0 |
| 131 | 2,6-diF | O | 4-n-Pentadecyl | 1.5352 |
| 132 | 2,6-diF | O | 4-O-n-Pentadecyl | 53.5–55.0 |
| 133 | 2,6-diF | O | 4-O-n-Hexadecyl | 66.0–70.0 |
| 134 | 2,6-diF | O | 4-O-n-Heptadecyl | 59.0–60.5 |
| 135 | 2,6-diF | O | 4-O-n-Nonadecyl | 61.0–61.5 |
| 136 | 2,6-diF | O | 4-O-n-Eicosyl | 38.5–39.0 |
| 137 | 2-Cl, 6-F | O | 4-$CH_2$-O-Et | 1.5604 |
| 138 | 2,6-diF | O | 4-$CH_2$-O-i-pr | 1.5340 |
| 139 | 2-Cl, 6-F | O | 4-$CH_2$-O-i-Pr | 1.5458 |
| 140 | 2,6-diF | O | 4-$CH_2$-O-i-Bu | 1.5372 |
| 141 | 2,6-diF | O | 4-OEt-O-Et | 1.5412 |
| 142 | 2,6-diF | O | 4-O-$C_4H_8$-O-i-Pr | 1.5316 |
| 143 | 2-Cl, 6-F | O | 4-O-Propargyl | 1.5807 |
| 144 | 2,6-diF | O | 4-O-Geraniol | 1.5482 |

TABLE 1-continued

| Compound No. | $R_1$, $R_2$ | Z | $R_3$, $R_4$ | Physical property value |
|---|---|---|---|---|
| 145 | 2,6-diF | O | 4-O-β-Citronellol | 1.5352 |
| 146 | 2,6-diF | O | 4-triMe-Silyl | 1.5444 |
| 147 | 2-Cl, 6-F | O | 4-triMe-Silyl | 1.5556 |
| 148 | 2,6-diF | O | 4-triEt-Silyl | 1.5444 |
| 149 | 2,6-diF | O | 4-t-Bu-diMe-Silyl | 1.5413 |
| 150 | 2,6-diF | O | 4-Cyclohexyl | 1.5586 |
| 151 | 2,6-diF | O | 4-Cyclohexyl(4-t-Bu) | 1.5428 |
| 152 | 2-Cl, 6-F | O | 4-Cyclohexyl(4-t-Bu) | 1.5486 |
| 153 | 2,6-diF | O | 4-Ph | 98.0–101.0 |
| 154 | 2-Cl, 4-F | O | 4-Ph | 88.0–92.0 |
| 155 | 2-Cl, 6-F | O | 4-Ph(2-Cl) | 1.6200 |
| 156 | 2,6-diF | O | 4-Ph(3-Cl) | 66.5–67.5 |
| 157 | 2,6-diF | O | 4-Ph(4-Cl) | 160.0–161.0 |
| 158 | 2-Cl, 6-F | O | 4-Ph(4-Br) | 101.0–102.0 |
| 159 | 2,6-diF | O | 4-Ph(2,4-diF) | 1.5886 |
| 160 | 2,6-diF | O | 4-Ph(2-F, 4-Cl) | 72.0–92.0 |
| 161 | 2-Cl, 6-F | O | 4-Ph(2-F, 4-Cl) | 77.0–95.0 |
| 162 | 2-Cl, 6-F | O | 4-Ph(2-F, 4-Br) | 1.6117 |
| 163 | 2,6-diF | O | 4-Ph(2-F, 4-Br) | 1.5998 |
| 164 | 2-Cl | O | 4-Ph(2,4-diCl) | 1.6468 |
| 165 | 2,6-diF | O | 4-Ph(2,4-diCl) | 1.6146 |
| 166 | 2,6-diF | O | 4-Ph(2-Cl, 4-Br) | 1.6140 |
| 167 | 2,6-diF | O | 4-Ph(3,4-diCl) | 114.0–115.0 |
| 168 | 2,6-diF | O | 4-Ph(3-Cl, 4-F) | 98.5–101.0 |
| 169 | 2-F | O | 4-Ph(4-OCF$_3$) | 79.0–85.0 |
| 170 | 2-Cl | O | 4-Ph(4-OCF$_3$) | 65.0–66.5 |
| 171 | 2-CF$_3$ | O | 4-Ph(4-OCF$_3$) | 74.0–76.0 |
| 172 | 2-OMe, 6-F | O | 4-Ph(4-OCF$_3$) | 78.0–80.0 |
| 173 | 2,6-diF | O | 4-Ph(4-OCF$_3$) | 1.5900 |
| 174 | 2-Cl, 6-F | O | 4-Ph(4-OCF$_3$) | 1.5990 |
| 175 | 2-Cl, 6-F | O | 4-Ph(2-Cl, 4-OCF$_3$) | 1.5702 |
| 176 | 2,6-diF | O | 4-Ph(2-Br, 4-OCF$_3$) | 1.5840 |
| 177 | 2,6-diF | O | 4-Ph(4-O-CH$_2$—CF$_3$) | 128.0–131.5 |
| 178 | 2-Cl, 6-F | O | 4-Ph(4-O-CH$_2$—CF$_3$) | 111.5–113.0 |
| 179 | 2,6-diF | O | 4-Ph(4-Me) | 123.0–127.0 |
| 180 | 2,6-diF | O | 4-Ph(4-Et) | 130.0–132.0 |
| 181 | 2-Cl, 6-F | O | 4-Ph(4-OEt) | 93.0–95.0 |
| 182 | 2,6-diF | O | 4-Ph(4-OEt) | 91.0–92.0 |
| 183 | 2,6-diF | O | 4-Ph(4-n-Pr) | 116.0–117.0 |
| 184 | 2,6-diF | O | 4-Ph(2-F, 4-n-Pr) | 1.5854 |
| 185 | 2,6-diF | O | 4-Ph(2-Cl, 4-n-Pr) | 1.5968 |
| 186 | 2,6-diF | O | 4-Ph(4-n-Bu) | 95.0–96.0 |
| 187 | 2,6-diF | O | 4-Ph(4-i-Bu) | 106.0–107.0 |
| 188 | 2,6-diF | O | 4-Ph(4-sec-Bu) | 1.5939 |
| 189 | 2,6-diF | O | 4-Ph(2-F, 4-t-Bu) | 1.5833 |
| 190 | 2,6-diF | O | 4-Ph(2-Me, 4-t-Bu) | 1.5828 |
| 191 | 2,6-diF | O | 4-Ph(4-n-Pentyl) | 60.0–62.0 |
| 192 | 2,6-diF | O | 4-Ph(4-i-Amyl) | 79.0–80.0 |
| 193 | 2,6-diF | O | 4-Ph(2-F, 4-n-Pentyl) | 69.5–71.0 |
| 194 | 2,6-diF | O | 4-Ph(4-n-Octyl) | 65.0–67.5 |
| 195 | 2,6-diF | O | 4-Ph(4-triMe-Silyl) | 1.5842 |
| 196 | 2-Cl, 6-F | O | 3-F, 4-Ph | 103.0–104.0 |
| 197 | 2,6-diF | O | 2-F, 4-Ph(4-Cl) | 112.0–116.0 |
| 198 | 2-Cl, 6-F | O | 2-F, 4-Ph(4-Cl) | 1.6168 |
| 199 | 2,6-diF | O | 2-F, 4-Ph(2,4-diCl) | 1.6062 |
| 200 | 2-Cl, 6-F | O | 2-F, 4-Ph(2,4-diCl) | 1.6101 |
| 201 | 2,6-diF | O | 2-F, 4-Ph(2-Me, 4-Cl) | 1.5961 |
| 202 | 2,6-diF | O | 2-F, 4-Ph(4-Et) | 99.5–100.0 |
| 203 | 2,6-diF | O | 2-F, 4-Ph(4-n-Pr) | 1.5771 |
| 204 | 2,6-diF | O | 2-F, 4-Ph(4-i-Pr) | 1.5961 |
| 205 | 2,6-diF | O | 2-F, 4-Ph(4-n-Pentyl) | 66.5–67.0 |
| 206 | 2,6-diF | O | 2-F, 4-Ph(2-OEt, 4-t-Bu) | 1.5722 |
| 207 | 2,6-diF | O | 2-F, 4-Ph(4-OCF$_3$) | 1.5656 |
| 208 | 2,6-diF | O | 2-Cl, 4-Ph(4-Cl) | 1.6229 |
| 209 | 2,6-diF | O | 2-Cl, 4-Ph(4-n-Pr) | 1.6005 |
| 210 | 2,6-diF | O | 2-Cl, 4-Ph(4-i-Pr) | 1.6017 |
| 211 | 2,6-diF | O | 2-Cl, 4-Ph(4-t-Bu) | 1.5900 |
| 212 | 2,6-diF | O | 2-Cl, 4-Ph(4-OCF$_3$) | 53.5–54.5 |
| 213 | 2,6-diF | O | 2-Me, 4-Ph(4-Et) | 114.0–115.0 |
| 214 | 2,6-diF | O | 2-Me, 4-Ph(4-t-Bu) | 1.5930 |
| 215 | 2,6-diF | O | 2-Me, 4-Ph(4-OCF$_3$) | 1.5648 |
| 216 | 2,6-diF | O | 2-Et, 4-Ph(4-OCF$_3$) | 1.5601 |
| 217 | 2,6-diF | O | 2-OMe, 4-Ph(4-OCF$_3$) | 1.5610 |
| 218 | 2-Cl, 6-F | O | 2-OMe, 4-Ph(4-OCF$_3$) | 89.5–91.0 |
| 219 | 2,6-diF | O | 2-OMe, 4-Ph(4-n-Pr) | 1.5852 |

TABLE 1-continued

| Compound No. | $R_1$, $R_2$ | Z | $R_3$, $R_4$ | Physical property value |
|---|---|---|---|---|
| 220 | 2,6-diF | O | 2-OEt, 4-Ph(4-Cl) | 1.6040 |
| 221 | 2,6-diF | O | 2-OEt, 4-Ph(4-OCF₃) | 1.5568 |
| 222 | 2,6-diF | O | 2-OEt, 4-Ph(4-i-Pr) | 1.5830 |
| 223 | 2-Cl, 6-F | O | 4-O-Pyridine | 1.6034 |
| 224 | 2-Cl, 6-F | O | 4-O-Pyridine(4-CF₃) | 89.0–89.5 |
| 225 | 2-Cl, 6-F | O | 3-OPh | 1.5995 |
| 226 | 2,6-diF | O | 4-OPh | 1.5923 |
| 227 | 2-Cl, 6-F | O | 4-OPh | 1.6023 |
| 228 | 2-Cl, 4-NO₂ | O | 4-OPh | 85.0–88.0 |
| 229 | 2,6-diMe | O | 4-OPh | 1.6024 |
| 230 | 2-Cl, 6-F | O | 4-OPh(4-Cl) | 1.5573 |
| 231 | 2,6-diF | O | 4-OPh(4-Br) | 1.5982 |
| 232 | 2-Cl, 6-F | O | 4-OPh(4-Br) | 1.6083 |
| 233 | 2,6-diF | O | 4-OPh(3-CF₃) | 1.5595 |
| 234 | 2,6-diF | O | 4-OPh(4-OCF₃) | 1.5437 |
| 235 | 2-Cl, 6-F | O | 4-OPh(4-OCF₃) | 1.5542 |
| 236 | 2,6-diF | O | 4-OPh(2-Cl, 4-CF₃) | 1.5846 |
| 237 | 2-Cl, 6-F | O | 4-OPh(2-Cl, 4-CF₃) | 1.5918 |
| 238 | 2,6-diF | O | 4-OPh(4-Me) | 1.5867 |
| 239 | 2-Cl, 6-F | O | 4-OPh(4-Me) | 1.5973 |
| 240 | 2,6-diF | O | 4-OPh(4-OMe) | 1.5891 |
| 241 | 2-Cl, 6-F | O | 4-OPh(4-OMe) | 54.0–57.0 |
| 242 | 2-Cl, 6-F | O | 4-OPh(4-n-Pr) | 1.5861 |
| 243 | 2-Br | O | 4-OPh(4-sec-Bu) | 1.6046 |
| 244 | 2,6-diF | O | 4-OPh(4-sec-Bu) | 1.5717 |
| 245 | 2-Cl, 6-F | O | 4-OPh(4-t-Bu) | 78.0–81.0 |
| 246 | 2,6-diF | O | 4-OPh(4-n-Hexyl) | 1.5621 |
| 247 | 2,6-diF | O | 4-OPh(3,5-diMe, 4-O-n-Octyl) | 1.5488 |
| 248 | 2,6-diF | O | 4-OPh(4-n-Dodecyl) | 1.5387 |
| 249 | 2,6-diF | O | 4-OPh(4-O-n-Dodecyl) | 43.0–44.0 |
| 250 | 2,6-diF | O | 2-F, 4-OPh(2-Cl, 4-CF₃) | 56.0–59.0 |
| 251 | 2-Cl, 6-F | O | 3-Cl, 4-OPh(4-Cl) | 1.6106 |
| 252 | 2-Cl, 6-F | O | 3-Me, 4-OPh(4-Me) | 1.5878 |
| 253 | 2,6-diF | O | 4-CH₂-Ph | 1.5924 |
| 254 | 2-Cl, 6-F | O | 4-CH₂-Ph | 1.6004 |
| 255 | 2,6-diF | O | 4-CH₂-Ph(4-F) | 1.5767 |
| 256 | 2,6-diF | O | 4-CH₂-Ph(4-Cl) | 1.5920 |
| 257 | 2,6-diF | O | 4-CH₂-Ph(2,4-diF) | 1.5719 |
| 258 | 2,6-diF | O | 4-CH₂-Ph(2,4-diCl) | 1.5982 |
| 259 | 2-Cl, 6-F | O | 4-CH₂-Ph(2,4-diCl) | 1.6078 |
| 260 | 2,6-diF | O | 4-CH₂-Ph(2,3,4,5,6-penta-F) | 1.5494 |
| 261 | 2,6-diF | O | 4-CH₂-Ph(4-OCF₃) | 1.5617 |
| 262 | 2-Cl, 6-F | O | 4-CH₂-Ph(4-OCF₃) | 1.5722 |
| 263 | 2,6-diF | O | 4-CH₂-Ph(4-OMe) | 1.5850 |
| 264 | 2,6-diF | O | 4-CH₂-Ph(4-Et) | 1.5795 |
| 265 | 2,6-diF | O | 4-CH₂-Ph(4-i-Pr) | 1.5824 |
| 266 | 2-Cl, 6-F | O | 4-CH₂-Ph(4-i-Pr) | 1.5956 |
| 267 | 2,6-diF | O | 4-CH₂-Ph(4-n-Bu) | 1.5682 |
| 268 | 2-Cl, 6-F | O | 4-CH₂-Ph(4-n-Bu) | 1.5750 |
| 269 | 2-Cl, 6-F | O | 4-CH₂-Ph(4-t-Bu) | 1.5835 |
| 270 | 2,6-diF | O | 4-CH₂-Ph(4-n-Hexyl) | 1.5585 |
| 271 | 2-Cl, 6-F | O | 4-CH₂-Ph(4-n-Hexyl) | 1.5702 |
| 272 | 2,6-diF | O | 4-CH₂-Ph(4-n-Octyl) | 1.5514 |
| 273 | 2-Cl, 6-F | O | 4-CH₂-Ph(4-n-Octyl) | 1.5620 |
| 274 | 2,6-diF | O | 2-F, 4-CH₂-Ph(4-Cl) | 1.5908 |
| 275 | 2,6-diF | O | 2-F, 4-CH₂-Ph(4-t-Bu) | 1.5632 |
| 276 | 2,6-diF | O | 2-F, 4-CH₂-Ph(4-n-Octyl) | 1.5464 |
| 277 | 2,6-diF | O | 2-Cl, 4-CH₂-Ph(4-n-Octyl) | 1.5474 |
| 278 | 2,6-diF | O | 4-C₂H₄-Ph(4-Cl) | 1.5869 |
| 279 | 2-Cl, 6-F | O | 4-C₂H₄-Ph(4-Cl) | 1.5968 |
| 280 | 2-Cl, 6-F | O | 4-CH(Me)-Ph(4-Et) | 1.5706 |
| 281 | 2,6-diF | O | 4-CH(i-Bu)-Ph(4-Cl) | 1.5768 |
| 282 | 2-Cl, 6-F | O | 4-CH(i-Bu)-Ph(4-Cl) | 1.5896 |
| 283 | 2,6-diF | O | 4-C(diMe)-Ph(4-Cl) | 1.5493 |
| 284 | 2-Cl, 6-F | O | 4-C(diMe)-Ph(4-n-Octyl) | 1.5421 |
| 285 | 2,6-diF | O | 2-F, 4-C(diMe)-Ph(4-Cl) | 1.5624 |
| 286 | 2,6-diF | O | 4-OCH₂-Ph | 69.0–72.0 |
| 287 | 2-Cl, 6-F | O | 4-OCH₂-Ph | 1.5965 |
| 288 | 2,6-diF | O | 4-OCH₂-Ph(2-Cl) | 1.5942 |
| 289 | 2-Cl, 6-F | O | 4-OCH₂-Ph(2-Cl) | 65.0–66.5 |
| 290 | 2,6-diF | O | 4-OCH₂-Ph(4-F) | 106.0–107.0 |
| 291 | 2,6-diF | O | 4-OCH₂-Ph(4-Cl) | 112.0–116.0 |
| 292 | 2-Cl, 6-F | O | 4-OCH₂-Ph(4-Cl) | 117.5–118.0 |
| 293 | 2,6-diF | O | 4-OCH₂-Ph(2,6-diF) | 1.5632 |
| 294 | 2-Cl, 6-F | O | 4-OCH₂-Ph(2,6-diF) | 1.5742 |

TABLE 1-continued

| Compound No. | $R_1, R_2$ | Z | $R_3, R_4$ | Physical property value |
|---|---|---|---|---|
| 295 | 2,6-diF | O | 4-OCH$_2$-Ph(2,3-diCl) | 1.5936 |
| 296 | 2,6-diF | O | 4-OCH$_2$-Ph(3,4-diCl) | 69.0–70.5 |
| 297 | 2-Cl, 6-F | O | 4-OCH$_2$-Ph(3,4-diCl) | 1.6049 |
| 298 | 2,6-diF | O | 4-OCH$_2$-Ph(3,5-diCl) | 76.0–78.0 |
| 299 | 2,6-diF | O | 4-OCH$_2$-Ph(4-CF$_3$) | 106.5–108.5 |
| 300 | 2,6-diF | O | 4-OCH$_2$-Ph(4-OCF$_3$) | 94.5–97.0 |
| 301 | 2,6-diF | O | 4-OCH$_2$-Ph(4-Et) | 105.0–106.5 |
| 302 | 2,6-diF | O | 4-OCH$_2$-Ph(4-i-Pr) | 1.5741 |
| 303 | 2,6-diF | O | 4-OCH$_2$-Ph(4-t-Bu) | 1.5649 |
| 304 | 2,6-diF | O | 4-OCH$_2$-Ph(4-n-Pentyl) | 77.5–78.5 |
| 305 | 2,6-diF | O | 3-Me, 4-OCH$_2$-Ph(4-Et) | 97.5–99.5 |
| 306 | 2-Cl, 6-F | O | 4-CH$_2$-O-Ph(4-Cl) | 111.0–113.0 |
| 307 | 2,6-diF | O | 4-O-C$_4$H$_8$-O-Ph(4-Cl) | 1.5678 |
| 308 | 2-Cl, 6-F | O | 4-O-C$_4$H$_8$-O-Ph(4-Cl) | 1.5598 |
| 309 | 2,6-diF | O | 4-Silyl(diMe)-Ph | 1.5778 |
| 310 | 2-OMe | S | H | 134.0–142.0 |
| 311 | 2,6-diF | S | 4-i-Pentyl | 58.5–60.5 |
| 312 | 2,6-diF | S | 4-n-Octyl | 1.5553 |
| 313 | 2,6-diF | S | 4-Ph(4-OCF$_3$) | 92.0–94.0 |
| 314 | 2,6-diF | S | 4-OPh(4-Me) | 61.0–63.0 |
| 315 | 2-Cl, 6-F | S | 4-CH$_2$-Ph(4-i-Pr) | 57.0–65.0 |
| 316 | 2,6-diF | S | 2-F, 4-CH$_2$-Ph(4-Cl) | 1.6166 |

TABLE 2

| Compound No. | $R_1, R_2$ | Z | A | $R_3, R_4$ | Physical property value |
|---|---|---|---|---|---|
| 317 | 2-Cl | O | —CH$_2$— | H | 90.0–93.0 |
| 318 | 2,6-diF | O | —CH$_2$— | 4-n-Octyl | 1.5274 |
| 319 | 2-Cl, 6-F | O | —CH$_2$— | 4-n-Octyl | 1.5354 |
| 320 | 2,6-diF | O | —CH$_2$— | 4-Ph | 1.6077 |
| 321 | 2-Cl | S | —CH$_2$— | 3-Cl | 68.5–71.0 |
| 322 | 2-Br | S | —CH$_2$— | H | 91.5–98.0 |
| 323 | 2-OMe | S | —CH$_2$— | 4-Me | 1.6040 |
| 324 | 2-OMe | S | —CH$_2$— | 3-Cl | 1.6249 |

As apparent from the later-described test examples, the compounds of the above formula (I) provided by this invention have an extremely excellent acaricidal effect, and can be used as an acaricide for control of mites which externally parasitize the skins, etc. of animals (livestock, poultry, pets, wild animals, birds, etc.), control of mites which parasitize dwelling environment such as houses and offices, for example house dust mites, etc.

As specific examples of mites and ticks as the target can be mentioned *Dermatophagoides farinae, Tyrophagus putrescentiae, Aieuroglyphus ovatus, Tarsonemus granarius, Haplochthonius simplex, Coamochthonius reticulalus, Ornithonyssus bacoti, Macrocheles muscaedomesticae, Rhipicephalus sanguineus, Haemaphysalis flava, Ixodes ovatus, Haemaphysalis longicornis, Haemaphysalis mageshimaensis*, etc.

As to the acaricide of this invention, the compounds represented by the formula (I) can be used as such, but they are usually utilized after they are carried on liquid carriers, solid carriers or gaseous carriers, and then emulsifiers, dispersants, wetting agents, propellants, stabilizers, and other various auxiliaries are added according to necessity to make the mixtures into various forms fit for the application areas and the application methods, for example powders, granules, emulsions, oil solutions, aerosols, paints, fumigants, etc.

The liquid carriers include solvents such as xylene, toluene, benzene, cyclohexane, acetone, alcohols, mineral oils, petroleum and water.

The solid carriers include vegetable powders such as soybean meal and wheat flour, and mineral fine powders such as diatom earth, talc, kaolin, bentonite and clay.

The emulsifiers and dispersants include soaps, polyoxyethylene fatty alcohol ethers, polyoxyethylene fatty acid esters, sulfate esters of higher alcohols, alkylarylsulfonate salts, etc.

The propellants include, for example, liquefied petroleum gases, dimethyl ether, fluorocarbons, etc.

The acaricide of this invention can further contain various insecticides, synergists, pest repellents, antioxidants, stabilizers, bactericides, fungicides, perfumes, etc.

The amount of the effective ingredient in the acaricide of this invention can suitably be determined in accordance with its formulation form, application method and application place, but in the case of use in the form of liquid formulations such as wettable powders and emulsions, the amount can be 0.1 to 50.0% by weight, preferably 1.0 to 20.0% by weight. Further, in the case of use in the form of solids such as powders, the amount can be 0.1 to 50.0% by weight, preferably 2.0 to 20.0% by weight.

The acaricide of this invention can be applied externally to animals to be treated by a means such as application, atomization, pour-on, painting or immersion; or can be applied to places in dwelling environment such as houses and offices, where mites parasitize or may parasitize, for example carpets, tatami mats, places where indoor dust gathers, etc.

Its dose is an acaricidally effective amount, and cannot be sweepingly described because it largely varies depending on its application target, its application place, etc., but its optimal application amount may readily be determined by a person skilled in the art by carrying out a small-scale experiment. If an example is given as a tentative standard, the dose can be 0.01 g or more, preferably in the range of 0.05 to 1.0 g as the amount of the effective ingredient per m$^2$ of the area to be treated.

EXAMPLE

Formulation examples of compounds of this invention and test examples of acaricides of this invention are shown below. However, carriers, surfactants, etc. to be added in the formulations of the invention are not limited those used in these formulation examples.

Formulation Example 1 (powder)

2 parts of a compound of this invention (Compound No. 47), 50 parts of talc and 48 parts of clay are uniformly mixed and ground to give a powder.

Formulation Example 2 (wettable agent)

20 parts of a compound of this invention (Compound No. 104), 5 parts of sodium dodecylbenzenesulfonate, 3 parts of polyoxyethylene nonyl phenyl ether, 30 parts of clay and 42 parts of diatom earth are uniformly mixed and ground to give a wettable agent.

Formulation Example 3 (emulsion)

78 parts of xylol is added to 1.0 part of a compound of this invention (Compound No. 173) and 12 parts of polyoxyethylene nonyl phenyl ether, and the mixture is made into an emulsion where the solutes are uniformly dissolved.

Test Example 1

An acetone solution of a test compound was mixed with a feed so that the concentration of the test compound in the resultant treated feed became 1,000 ppm. 10 g of the treated feed was put in a 100-ml vial, *Tyrophagus putrescentiae* in the number of about 1,000 or *Dermatophagoides farinae* in the number of about 1,000 was inoculated thereon, and the vial was covered with a sheet of filter paper. Three weeks after the inoculation, the number of the living mites on the feed was counted about each kind of the mites according to the saline floating method. The effect of each of the chemicals tested was evaluated by calculating the proliferation rate according to the following equation; and grading the chemicals into 6 groups, namely grading rank A to a chemical among the above chemicals which gives a proliferation rate of 0 or more and under 5, grading rank B to a chemical which gives a proliferation rate of 5 or more and under 10, grading rank C to a chemical which gives a proliferation rate of 10 or more and under 20, grading rank D to a chemical which gives a proliferation rate of 20 or more and under 50, grading rank E to a chemical which gives a proliferation rate of 50 or more and under 90, and grading rank F to a chemical which gives a proliferation rate of 90 or more. The effect of rank A is the highest and the effect of rank F is the lowest.

Proliferation rate(%)=$C_1/C_2 \times T_2/T_1 \times 100$ $C_1$: number of mites released in the untreated section $C_2$: number of living mites at the time of investigation in the untreated section $T_1$: number of mites released in the treated section $T_2$: number of living mites at the time of investigation in the treated section As a result, high activities were observed, namely of B in respect of 1, 2, 4, 5, 7, 9, 10, 27, 37, 38, 134, 135, 136, 144, 228, 248, 310, 317, 320, 321, 322, 323 and 324 among the exemplified compounds (exemplified compound numbers 1 to 324), and of A in respect of all the other exemplified compounds.

Test Example 2

Eggs (about 50 eggs) of *Haemaphysalis longicornis* were placed on a sheet of filter paper treated with an acetone solution of a test compound so that the amount of the test compound became 500 μg/cm$^2$, and contacted with the sheet all day and night. The treated eggs were preserved in a 100-ml vial, and 5 weeks later hatch rates were investigated.

Ovicidal rate (%) =

$$\frac{\text{(Number of eggs used} - \text{Number of hatched larvae)}}{\text{Number of eggs used}} \times 100$$

As a result, all of the exemplified compounds (exemplified compound numbers 1 to 324) exhibited a high ovicidal effect of 90 to 100%.

We claim:

1. A method for control of ticks which externally parasitize pets or wild animals or birds, which method comprises applying an acaricidally effective amount of an oxazoline compound to the pets or wild animals or birds, said compound represented by the following formula

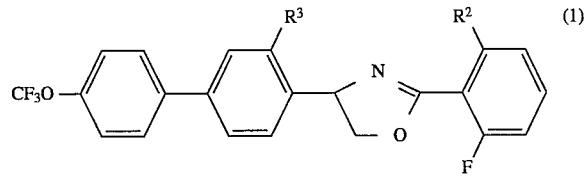

wherein

R$^3$ denotes a fluorine atom, a chlorine atom, a C$_1$ to C$_{15}$ alkyl group or a C$_1$ to C$_{15}$ alkoxy group, and R$^2$ denotes a fluorine atom or a chlorine atom.

2. A method according to claim 1 wherein R$^3$ denotes a fluorine atom and R$^2$ denotes a fluorine atom.

3. A method according to claim 1 wherein R$^3$ denotes a methyl group and R$^2$ denotes a fluorine atom.

* * * * *